United States Patent [19]

Horodysky et al.

[11] 4,370,248

[45] Jan. 25, 1983

[54] BORATED HYDROXYL-CONTAINING ACID ESTERS AND LUBRICANTS CONTAINING SAME

[75] Inventors: Andrew G. Horodysky, Cherry Hill; Joan M. Kaminski, Clementon, both of N.J.

[73] Assignee: Mobil Oil Corporation, New York, N.Y.

[21] Appl. No.: 216,881

[22] Filed: Dec. 16, 1980

Related U.S. Application Data

[63] Continuation-in-part of Ser. No. 132,023, Mar. 20, 1980, abandoned.

[51] Int. Cl.$^3$ .................. C07F 5/04; C10M 1/54
[52] U.S. Cl. ............... 252/49.6; 260/462 R; 260/410.6; 260/410.7; 260/410.8
[58] Field of Search ............ 252/49.6; 260/462 R, 260/410.6, 410.7

[56] References Cited

U.S. PATENT DOCUMENTS

| | | | |
|---|---|---|---|
| 2,469,370 | 5/1949 | Colbeth | 260/462 R X |
| 2,508,924 | 5/1950 | Mertens et al. | 260/462 R X |
| 3,067,192 | 12/1962 | Emrick | 260/462 R X |
| 3,150,157 | 9/1964 | Liao | 260/462 R X |
| 3,533,945 | 10/1970 | Vogel | 252/49.6 |
| 3,544,614 | 12/1970 | Schwartz | 260/462 R |
| 3,772,357 | 11/1973 | Hamanaka | 260/462 R X |

*Primary Examiner*—Paul F. Shaver
*Attorney, Agent, or Firm*—Charles A. Huggett; Michael G. Gilman; Claude E. Setliff

[57] ABSTRACT

Lubricating oils containing certain borated derivatives of hydroxyl-containing acid esters have been found to be effective friction modifiers and to aid in the reduction of fuel consumption in internal combustion engines.

19 Claims, No Drawings

BORATED HYDROXYL-CONTAINING ACID ESTERS AND LUBRICANTS CONTAINING SAME

CROSS REFERENCE TO RELATED APPLICATIONS

This application is a continuation-in-part of U.S. application Ser. No. 132,023, filed Mar. 20, 1980, now abandoned.

BACKGROUND OF THE INVENTION

1. Field of the Invention

The invention relates to new compositions and lubricating oils containing same. In particular, it relates to borated derivatives of hydroxyl-containing acid esters and their use in lubricating oils to reduce friction and fuel consumption in internal combustion engines.

2. Discussion of the Prior Art

So far as is known, no effort has been made to employ borated hydroxyl-containing acid esters as a lubricant additive or in sufficient amounts that it contributes to the lubricating properties of the blend. U.S. Pat. No. 2,788,326 discloses some of the esters suitable for the present invention, e.g. glycerol monooleate, as minor components of lubricating oil compositions. U.S. Pat. No. 3,235,498 discloses, among others, the same ester as just mentioned, as an additive to other oils. U.S. Pat. No. 2,443,578 teaches esters wherein the free hydroxyl is found in the acid portion, as for example in tartaric acid.

The above patents, as are numerous others, are directed to the use of such esters as additives. Other patents, such as U.S. Pat. Nos. 2,798,083; 2,820,014; 3,115,519; 3,282,971; and 3,309,318 as well as an article by R. S. Barnes et al. entitled "Synthetic Ester Lubricants" in Lubrication Engineering, August, 1957, pp. 454-457, teach lubricants prepared from polyhydric alcohols and acid containing no hydroxyl other than those associated with the acid function. However, all these references teach lubricants prepared from the fully esterified material.

In addition to the references already mentioned, the following patents are also of interest. U.S. Pat. No. 2,469,370 concerns boration of esters obtained from mono- or dihydric alcohols and fatty acids. U.S. Pat. No. 3,067,192 teaches borated acylated derivatives of polysaccharides. U.S. Pat. No. 3,150,157 relates to borated mono-acylated esters. U.S. Pat. No. 3,544,614 is concerned with complex esters for use in lubricants, the esters, in one aspect, being prepared by reacting boric acid, a polyhydric alcohol and a dicarboxylic acid or anhydride. U.S. Pat. Nos. 3,533,945 and 3,772,357 does relate to borated esters, the former teaching the ester to be one made by reacting a succinic acid-producing compound and a di- or polyhydric alcohol. The latter patent discloses, as prior art, the compound

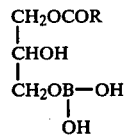

SUMMARY OF THE INVENTION

In accordance with the invention, there is provided a product obtained by reacting a hydroxyl-containing ester oil of lubricating viscosity with a boron compound, such as boric acid or a trialkyl borate. The invention also provides a lubricating oil composition comprising lubricating oil and the product. In such compositions, the product can be used in friction reducing amounts, which can range from about 0.1% by weight to about 90% by weight. It will be noted that this range embraces not only additive amounts, but also replacement amounts. The borated products also have significantly higher viscosity indices and good low temperature characteristics when used in either low additive concentrations or higher fluid replacement amounts when compared to the non-borated hydroxy-containing ester.

BACKGROUND OF THE INVENTION

The synthetic ester fluids are made by reacting a monocarboxylic acid and a polyhydric alcohol, chosen and selectively reacted so that the product of reaction will contain at least one, but not more than two, free hydroxyl groups. Further, the ester formed from the acid and polyhydride alcohol must have at least 2 ester groups.

The typical polyhydric alcohols contemplated for use in this invention are branched aliphatic polyhydric alcohols which include those containing from 3 to 30 carbon atoms and from 3 to 4 hydroxyls. Specific members that may be mentioned are the trimethylolalkanes, such as trimethylolpropane; pentaerythritol; dipentaerythritol; and the like. Thus, the ester is made by reacting 1 mole of $R(OH)_x$ with y moles of $R'COOH$, where x is 3 or 4 and y is 2 or 3, y being 2 when x is 3 or 4 and 3 only when x is 4.

The acids useful as reactants with these alcohols include any monocarboxylic acid of the formula

wherein R is a straight or branched chain hydrocarbyl group containing from 5 to 30 carbon atoms or mixtures thereof, but no alcoholic hydroxyl group. A particularly effective acid, or acid mixture, may be found among those having from 4 to 30 carbon atoms. Some of the acids that may be named are valeric, hexanoic (caproic), haptanoic, octanoic, nonanoic (pelargonic), decanoic (capric), pivalic (2,2-dimethylpropionic) myristic, oleic and stearic acids and the like. The hydrocarbyl is preferably an alkyl, but also includes alkenyl, cycloalkyl, cycloalkenyl, aralkyl and alkaryl, where the aryl portion contains 6-10 carbon atoms.

Among the esters contemplated are pentaerythritol di- and tributyrate esters, the pentaerythritol di- and trioleate ester, the pentaerythritol di- and tricaproate esters, and the pentaerythritol di- and triesters wherein the acids are selected from mixed $C_5$-$C_{18}$ acids, e.g. mixtures of pelargonic and oleic acids. Included also are the diesters of trimethylolpropane and pivalic, valeric, caproic, heptanoic, octanoic or nonanoic acids, or mixtures thereof, and the like.

The ester used in this invention can be made up of a single ester or it can include two or more esters. Such a mixture can contain from about 5% to about 95% by weight of any one ester, the other ester or esters being selected such that it or they together comprise from about 95% to about 5% by weight.

The synthesis of these esters is well known in the prior art and is not a part of the present invention. Generally, they may be made by reacting alcohol and either of the acids at from about 100° C. to about 300° C. for from about 2 hours to about 20 hours. The temperature selected and the time required will depend in large measure on the particular reactants chosen, as will be readily understood by those in this art.

As has been said, reactant proportions must be chosen such that the ester will contain at least one, but not more than two, free hydroxyl groups. If no free hydroxy group remains on some molecules, those fully esterified esters will be carried along as a diluent in the boration reaction to form a mixture of borated hydroxyl-containing ester and diluent non-hydroxyl-containing ester. For example, if pentaerythritol is chosen, no more than three moles of acid will be used. If trimethylolpropane is chosen, no more than two moles of acid will be used.

The borated derivatives can be prepared by several known methods. These include treatment with boric acid (with removal of water as it is formed) or treatment with an alkyl borate, such a tributyl borate, and removing the alcohol as the transesterification reaction progresses. Other methods can also be used.

Treatment with boric acid can be performed in the presence of an alcoholic solvent, such as butanol or pentanol, or a hydrocarbon solvents such as benzene, toluene or xylene, or mixtures of such solvents. Reaction temperatures of 70° C. to 250° C. or more can be used, but 120° to 170° C. is preferred. Reaction times can be 1 to 10 hours and more. Up to a stoichiometric amount of boric acid can be used, or an excess of boric acid can be used to produce a derivative containing from about 0.05% to 6% boron. The hydroxy-esters can also be borated through transesterification with a trialkyl borate such as tributyl borate, often in the presence of boric acid. Preferred reaction temperatures often range from 180° C. to 280° C. in order to drive off the alcohol derived from the trialkyl borate. Again, times can be from 1 to 10 hours, or more.

The alkyl borate is one of the formula

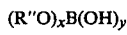
(R″O)$_x$B(OH)$_y$ where R″ is a $C_1$ to $C_6$ alkyl, x is 1 to 3 and y is 0, 1 or 2.

As disclosed hereinabove, the borated ester fluid is used with lubricating oils to the extent of from about 0.1% to about 90% by weight of the total composition. Furthermore, other additives, such as detergents, antioxidants, antiwear agents and the like may be present.

The lubricating oils contemplated for use with the esters herein disclosed include both mineral and synthetic hydrocarbon oils of lubricating viscosity and mixtures thereof with other synthetic oils. The synthetic hydrocarbon oils include long chain alkanes such as cetanes and olefin polymers such as oligomers of hexene, octene, decene, and dodecene, etc. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

In all reactions, described hereinabove, a solvent is preferred. Solvents that can be used include the hydrocarbon solvents, such as toluene, benzene, xylene, and the like.

Having described the invention in general terms, the following are offered to specifically illustrate the development. It is to be understood they are illustrations only and that the invention shall not be limited except as limited by the appended claims.

EXAMPLE 1

A mixture of 1 mole of pentaerythritol, 1.5 moles of oleic acid and 0.5 mole of pelargonic acid was heated in the presence of a catalytic amount of p-toluene sulfonic acid (0.1% of the combined weight of reactants) at a temperature of 240° C. Water was simultaneously removed, and the reaction was continued until an acid number of less than 1 was obtained. The partial ester was filtered to yield a clear ester containing 2 free hydroxyl groups.

EXAMPLE 2

Approximately 3310 parts of the hydroxyl-containing ester described in Example 1, 185 parts of boric acid and 300 parts of toluene were charged to a stirred reactor equipped with a Dean-Stark tube. The reactants were heated at 160° C. over a period of about 5 hours until water evolution stopped. Approximately 45 parts of butanol were added and the mixture was held at 155°–165° C. for an additional hour. The solvents were removed by vacuum distillation and the borated fluid was filtered over diatomaceous earth to form a clear, orange-brown liquid.

EXAMPLE 3

This hydroxyl-containing ester was synthesized as generally described in Example 1 using, for each mole of pentaerythritol, 0.5 mole of oleic acid and 2 moles of pelargonic acid, to form a hydroxyl-containing ester with 1.5 free hydroxyl groups.

EXAMPLE 4

Approximately 4195 parts of hydroxyl-containing ester described in Example 3, 235 parts of boric acid and 300 parts of toluene were charged to a stirred reactor equipped with a Dean-Stark tube. The reactants were heated to 170° C. and heating at this temperature was continued over a period of about 6 hours until water evolution stopped. The solvent was removed by vacuum distillation and the fluid was filtered over diatomaceous earth to remove any excess boric acid. The product was a clear, orange-brown fluid.

EXAMPLE 5

This hydroxyl-containing ester was synthesized as generally described in Example 1, using for each mole of pentaerythritol, 3 moles oleic acid, to form a hydroxyl-containing pentaerythritol trioleate with 1 free hydroxyl group.

EXAMPLE 6

Approximately 2170 parts of the hydroxyl-containing ester described in Example 5, 165 parts of boric acid and 150 parts of toluene were charged to a stirred reactor equipped with a Dean-Stark tube. The reaction mixture was heated to 180° C., and heating at 180° C. was continued for a period of about 8 hours until water evolution ended. The solvent was removed by vacuum distillation and the crude product was filtered through diatomaceous earth to remove excess boric acid. The product was a clear, orange-brown liquid.

EXAMPLE 7

Approximately 2785 parts of the hydroxyl-containing ester described in Example 5 was borated with 62 parts of boric acid in about 175 parts of toluene and about 30 parts of butanol in a manner similar to that described in Example 6, but using less boric acid. The reactants were heated in 155°–160° C. and held there for a period of 4.5 hours until water evolution ended. The solvents were removed by vacuum distillation and the liquid was filtered through diatomaceous earth. The product was a clear, orange-brown liquid.

EXAMPLE 8

This hydroxyl group ester was synthesized as generally described in Example 1, using, for each mole of trimethylolpropane, 1 mole of oleic acid and 1 mole of pelargonic acid, to form a hydroxyl-containing ester with 1 free hydroxyl group.

EXAMPLE 9

Approximately 2035 parts of the hydroxyl-containing ester described in Example 8 was borated with 77 parts of boric acid and about 220 parts of toluene in a stirred reactor equipped with a Dean-Stark tube. After a 5 hour reaction period at 155°–165° C., the water evolution terminated. The solvent was removed by vacuum distillation and the liquid was filtered through diatomaceous earth. The product was a clear, orange-brown, low viscosity fluid.

EVALUATION OF PRODUCTS

The compounds were evaluated as friction modifiers in accordance with the following test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$. Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4–8 microinches.

The data obtained are shown in Table 1. The data in Table 1 are reported as percent reduction in coefficient of friction at two speeds. The friction-reducing ester additives were evaluated in a fully formulated 5W-20 synthetic lubricating oil comprising an additive package including antioxidant, detergent and dispersant. The oil had the following general characteristics:

| Viscosity @ 100° C. | 6.8 cs |
| Viscosity @ 40° C. | 36.9 cs |
| Viscosity Index | 143 |

TABLE 1

| Test Oil | Moles of Polyol | Composition of Ester Fluid | | | Ester Conc., % Wt. | % Change in Coefficient of Friction at | |
| | | Moles of Oleic Acid | Moles of Pelargonic Acid | Free OH Groups Present | | 5 ft./min. | 30 ft./min. |
|---|---|---|---|---|---|---|---|
| Base Oil (SAE 5W-20) | | | | | 0 | 0 | 0 |
| Base Oil plus Ex. 1 | 1-PE | 1.5 | 0.5 | 2 | 20 | 19 | 18 |
| Base Oil plus Ex. 2 | 1-PE | 1.5 | 0.5 | Borated | 20 | 49 | 34 |
| | | | | | 4 | 29 | 22 |
| Base Oil plus Ex. 3 | 1-PE | 0.5 | 2 | 1.5 | 20 | 21 | 18 |
| Base Oil plus Ex. 4 | 1-PE | 0.5 | 2 | Borated | 20 | 43 | 31 |
| Base Oil plus Ex. 4 | | | | | 4 | 28 | 21 |
| Base Oil plus Ex. 5 | 1-PE | 3 | 0 | 1 | 20 | 32 | 21 |
| Base Oil plus Ex. 6 | 1-PE | 3 | 0 | Borated | 20 | 51 | 38 |
| Base Oil plus Ex. 6 | | | | | 4 | 26 | 18 |
| Base Oil plus Ex. 7 | 1-PE | 3 | 0 | Borated | 4 | 32 | 23 |
| | | | | | 2 | 32 | 22 |
| Base Oil plus Ex. 8 | 1-TMP | 1 | 1 | 1 | 20 | 7 | 20 |
| Base Oil plus Ex. 9 | 1-TMP | 1 | 1 | Borated | 20 | 29 | 26 |
| | | | | | 4 | 15 | 17 |

PE is pentaerythritol
TMP is trimethylolpropane

We claim:

1. A product of reaction obtained by initially reacting (1) a branched aliphatic polyhydric alcohol containing 3 or 4 hydroxyl groups with a monocarboxylic acid such that the initial compound has 2 or 3 acyl groups, 2 when the alcohol has 3 or 4 hydroxyl groups and 3 only when the alcohol has 4 hydroxyl groups and then reacting the ester obtained with (2) a boron compound.

2. The product of claim 1 wherein the polyhydric alcohol contains from 3 to 30 carbon atoms and the monocarboxylic has the formula

R—COOH wherein R is a hydrocarbyl group containing 5 to 30 carbon atoms, or mixtures of such hydrocarbyl groups.

3. The product of claim 1 wherein the boron compound is boric acid.

4. The product of claim 1 wherein the boron compound has the formula $(R''O)_x B(OH)_y$ wherein R'' is a $C_1$ to $C_6$ alkyl, x is 1 to 3 and y is 0, 1 or 2.

5. The product of claim 4 wherein the boron compound is a trialkyl borate.

6. The product of claim 1 wherein boric acid is reacted with an ester prepared from pentaerythritol, oleic acid and pelargonic acid, said ester having 2 free hydroxyl groups per molecule.

7. The product of claim 1 wherein boric acid is reacted with an ester prepared from pentaerythritol, oleic acid and pelargonic acid, said ester having 1.5 free hydroxyl groups per molecule.

8. The product of claim 1 wherein boric acid is reacted with an ester prepared from pentaerythritol, oleic acid and pelargonic acid, said ester having 1 free hydroxyl group per molecule.

9. The product of claim 1 wherein boric acid is reacted with an ester prepared from trimethylolpropane, oleic acid and pelargonic acid, said ester having 1 free hydroxyl group per molecule.

10. A lubricant composition comprising lubricant and a friction reducing amount of a product of reaction obtained by initially reacting (1) a branched aliphatic polyhydric alcohol containing 3 or 4 hydroxyl groups with a monocarboxylic acid such that the initial compound has 2 or 3 acyl groups, 2 when the alcohol has 3 or 4 hydroxyl groups and 3 only when the alcohol has 4 hydroxyl groups and then reacting the ester obtained with (2) a boron compound.

11. The composition of claim 10 wherein the ester is obtained from a polyhydric alcohol having from 3 to 30 carbon atoms and a monocarboxylic acid of the formula

R—COOH wherein R is a hydrocarbyl group containing 5 to 30 carbon atoms, or mixtures of such hydrocarbyl groups.

12. The composition of claim 10 wherein the boron compound is boric acid.

13. The composition of claim 10 wherein the boron compound has the formula $(R''O)_x B(OH)_y$ wherein R'' is a $C_1$ to $C_6$ alkyl, x is 1 to 3 and y is 0, 1 or 2.

14. The composition of claim 13 wherein the boron compound is a trialkyl borate.

15. The composition of claim 10 wherein the product of reaction is obtained by reacting boric acid with an ester prepared from pentaerythritol, oleic acid and pelargonic acid, said ester having 2 free hydroxyl groups per molecule.

16. The composition of claim 10 wherein the product of reaction is obtained by reacting boric acid with an ester prepared from pentaerythritol, oleic acid and pelargonic acid, said ester having 1.5 free hydroxyl group per molecule.

17. The composition of claim 10 wherein the product of reaction is obtained by reacting boric acid with an ester prepared from pentaerythritol, oleic acid and pelargonic acid, said ester having 1 free hydroxyl group per molecule.

18. The composition of claim 10 wherein the product of reaction is obtained by reacting boric acid with an ester prepared from trimethylolpropane, oleic acid and pelargonic acid, said ester having 1 free hydroxyl group per molecule.

19. The product of claim 1 wherein boric acid is reacted with the ester prepared from pentaerythritol and oleic acid.

20. The composition of Claim 10 wherein the lubricant is a mineral oil.

21. The composition of Claim 10 wherein the lubricant is a mixture of mineral and synthetic lubricating oils.

* * * * *

UNITED STATES PATENT AND TRADEMARK OFFICE
CERTIFICATE OF CORRECTION

PATENT NO. : 4,370,248

DATED : January 25, 1983

INVENTOR(S) : Andrew G. Horodysky et al

It is certified that error appears in the above-identified patent and that said Letters Patent is hereby corrected as shown below:

Column 2, line 45, "haptanoic" should be -- heptanoic --.

Column 7, line 11, Claim 2, "carboxylic has" should be -- carboxylic acid has --.

Signed and Sealed this

Twenty-fourth Day of May 1983

[SEAL]

Attest:

DONALD J. QUIGG

Attesting Officer

Acting Commissioner of Patents and Trademarks